US011014870B2

(12) United States Patent
Chang et al.

(10) Patent No.: US 11,014,870 B2
(45) Date of Patent: *May 25, 2021

(54) PROCEDURE FOR THE PREPARATION OF 4-PHENYL BUTYRATE AND USES THEREOF

(71) Applicant: Horizon Therapeutics, LLC, Lake Forest, IL (US)

(72) Inventors: Huai-Chueh Chang, Tower Lakes, IL (US); Steven S. Pfeiffer, Camarillo, CA (US); Vasilios H. Iskos, Chicago, IL (US); Maki Uragami, Bethlehem, PA (US); Steven Weissman, Short Hills, NJ (US); Andrew Thompson, Mountainside, NJ (US)

(73) Assignee: Horizon Therapeutics, LLC, Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/405,523

(22) Filed: May 7, 2019

(65) Prior Publication Data

US 2020/0002266 A1    Jan. 2, 2020

Related U.S. Application Data

(63) Continuation of application No. 15/696,448, filed on Sep. 6, 2017, now Pat. No. 10,329,236, which is a continuation of application No. 15/164,126, filed on May 25, 2016, now Pat. No. 9,914,692.

(51) Int. Cl.
| | |
|---|---|
| *C07C 69/616* | (2006.01) |
| *C07C 51/60* | (2006.01) |
| *C07C 51/29* | (2006.01) |
| *C07C 57/30* | (2006.01) |
| *C07C 67/14* | (2006.01) |

(52) U.S. Cl.
CPC ............ *C07C 69/616* (2013.01); *C07C 51/29* (2013.01); *C07C 51/60* (2013.01); *C07C 57/30* (2013.01); *C07C 67/14* (2013.01)

(58) Field of Classification Search
CPC ......... C07C 51/29; C07C 51/60; C07C 57/30; C07C 67/14; C07C 69/616
See application file for complete search history.

(56) References Cited

U.S. PATENT DOCUMENTS

| | | | |
|---|---|---|---|
| 3,686,238 A | 8/1972 | Zaffaroni | |
| 4,284,647 A | 8/1981 | Brusilow | |
| 4,457,942 A | 7/1984 | Brusilow | |
| 5,654,333 A | 8/1997 | Samid | |
| 5,968,979 A | 10/1999 | Brusilow | |
| 6,060,510 A | 5/2000 | Brusilow | |
| 6,083,984 A | 7/2000 | Brusilow | |
| 6,219,567 B1 | 4/2001 | Eggers | |
| 6,372,938 B1 * | 4/2002 | Burzynski | ............ C07C 51/353 |
| | | | 562/465 |
| 6,825,384 B1 | 11/2004 | Prakash | |
| 8,053,581 B2 * | 11/2011 | Li | ......................... C07D 277/24 |
| | | | 548/195 |
| 8,094,521 B2 | 1/2012 | Levy | |
| 8,404,215 B1 | 3/2013 | Scharschmidt | |
| 8,642,012 B2 | 2/2014 | Scharschmidt | |
| 9,078,865 B2 | 7/2015 | Lee | |
| 9,095,559 B2 | 8/2015 | Scharschmidt | |
| 9,254,278 B2 | 2/2016 | Scharschmidt | |
| 9,289,406 B2 | 3/2016 | Scharschmidt | |
| 9,326,966 B2 | 5/2016 | Scharschmidt | |
| 9,561,197 B2 | 2/2017 | Scharschmidt | |
| 9,914,692 B2 | 3/2018 | Chang | |
| 9,962,358 B2 | 5/2018 | Scharschmidt | |
| 9,962,359 B2 | 5/2018 | Scharschmidt | |
| 9,999,608 B2 | 6/2018 | Scharschmidt | |
| 10,045,958 B1 | 8/2018 | Scharschmidt | |
| 10,045,959 B1 | 8/2018 | Scharschmidt | |
| 10,183,002 B2 | 1/2019 | Scharschmidt | |
| 10,183,003 B2 | 1/2019 | Scharschmidt | |
| 10,183,004 B2 | 1/2019 | Scharschmidt | |
| 10,183,005 B2 | 1/2019 | Scharschmidt | |
| 10,183,006 B2 | 1/2019 | Scharschmidt | |
| 10,329,236 B2 | 6/2019 | Chang | |

(Continued)

FOREIGN PATENT DOCUMENTS

| | | |
|---|---|---|
| CN | 1778963 | 5/2006 |
| CN | 103304402 A | 9/2013 |

(Continued)

OTHER PUBLICATIONS

National Center for Biotechnology Information. PubChem Database. 4-Phenylbutyric acid, CID=4775, https://pubchem.ncbi.nlm.nih.gov/compound/4-Phenylbutyric-acid (accessed on Mar. 22, 2020; create date Mar. 25, 2005) (Year: 2005).*

Gill et al., "Differential Scanning Calorimetry Techniques: Applications in Biology and Nanoscience", 2010, J. Biomol. Tech., 21(4), pp. 167-193. (Year: 2010).*

Shibuya et al., "Organocatalytic One-Pot Oxidative Cleavage of Terminal Diols to Dehomologated Carboxylic Acids", 2012, Organic Letters, 14(19), pp. 5006-5009. (Year: 2012).*

Bigot, A. et al., "Liver Involvement in Urea Cycle Disorders: A Review of the Literature", J Inherit Metab Dis., (Abstract only), 40(6):757-69, (2017).

European Medicines Agency Assessment Report for Ravicti (Year: 2015).

"Program for SIMD annual meeting", Molecular Genetics and Metabolism, (Mar. 1, 2012), vol. 105, No. 3, doi:10.1016/j.ymgme.2012.01.004, ISSN 1096-7192, pp. 273-366, XP055202401.

(Continued)

*Primary Examiner* — My-Chau T. Tran
(74) *Attorney, Agent, or Firm* — Chris Marion; Stephanie M. Greer

(57) ABSTRACT

Provided is a process for preparing 4-phenyl-1-butyric acid, comprising: reacting 4-phenyl-1-butanol with sodium chlorite, a nitroxyl radical catalyst and sodium hypochlorite in an organic solvent and a phosphate buffer; and quenching the reaction with sodium sulfite to produce 4-phenyl-1-butyric. Also provided is 4-phenyl-1-butyric acid prepared by such a process.

5 Claims, No Drawings

(56) References Cited

U.S. PATENT DOCUMENTS

| | | |
|---|---|---|
| 2003/0195255 A1 | 10/2003 | Summar |
| 2004/0229948 A1 | 11/2004 | Summar |
| 2005/0273359 A1 | 12/2005 | Young |
| 2006/0135612 A1 | 6/2006 | Ferrante |
| 2008/0119554 A1 | 5/2008 | Jalan |
| 2010/0008859 A1 | 1/2010 | Scharschmidt |
| 2010/0016207 A1 | 1/2010 | Vvurtman |
| 2012/0022157 A1 | 1/2012 | Scharschmidt |
| 2012/0220661 A1 | 8/2012 | Lee |
| 2013/0085179 A1 | 4/2013 | Scharschmidt |
| 2013/0172543 A1 | 7/2013 | Iwabuchi |
| 2013/0210914 A1 | 8/2013 | Scharschmidt |
| 2013/0281530 A1 | 10/2013 | Scharschmidt |
| 2014/0142186 A1 | 5/2014 | Scharschmidt |
| 2014/0256807 A1 | 9/2014 | Scharschmidt |
| 2015/0094278 A1 | 4/2015 | Scharschmidt |
| 2015/0105469 A1 | 4/2015 | Scharschmidt |
| 2015/0335605 A1 | 11/2015 | Scharschmidt |
| 2016/0074356 A1 | 3/2016 | Scharschmidt |
| 2016/0081969 A1 | 3/2016 | Scharschmidt |
| 2016/0199332 A1 | 7/2016 | Scharschmidt |
| 2016/0199333 A1 | 7/2016 | Scharschmidt |
| 2016/0199334 A1 | 7/2016 | Scharschmidt |
| 2016/0202240 A1 | 7/2016 | Scharschmidt |
| 2016/0223520 A1 | 8/2016 | Scharschmidt |
| 2016/0354025 A1 | 12/2016 | Scharschmidt |
| 2017/0266143 A1 | 9/2017 | Scharschmidt |
| 2017/0348269 A1 | 12/2017 | Scharschmidt |
| 2017/0354631 A1 | 12/2017 | Scharschmidt |
| 2017/0354632 A1 | 12/2017 | Scharschmidt |
| 2018/0015058 A1 | 1/2018 | Scharschmidt |
| 2018/0015064 A1 | 1/2018 | Scharschmidt |
| 2018/0015065 A1 | 1/2018 | Scharschmidt |
| 2018/0017546 A1 | 1/2018 | Scharschmidt |
| 2018/0021291 A1 | 1/2018 | Scharschmidt |
| 2018/0021292 A1 | 1/2018 | Scharschmidt |
| 2018/0021293 A1 | 1/2018 | Scharschmidt |
| 2018/0055807 A1 | 3/2018 | Scharschmidt |
| 2018/0263938 A1 | 9/2018 | Scharschmidt |
| 2019/0076383 A1 | 3/2019 | Scharschmidt |
| 2019/0076384 A1 | 3/2019 | Scharschmidt |
| 2019/0076386 A1 | 3/2019 | Scharschmidt |
| 2019/0125713 A1 | 5/2019 | Scharschmidt |

FOREIGN PATENT DOCUMENTS

| | | |
|---|---|---|
| EP | 2607366 A1 | 6/2013 |
| IT | 1317073 B1 | 5/2003 |
| JP | 2012501329 | 1/2012 |
| WO | 199422494 | 10/1994 |
| WO | 1996024571 | 8/1996 |
| WO | 2005053607 A2 | 6/2005 |
| WO | 2006056794 A1 | 6/2006 |
| WO | 2007005633 A2 | 1/2007 |
| WO | 2009087474 A2 | 7/2009 |
| WO | 2009134460 | 11/2009 |
| WO | 2009134460 A1 | 11/2009 |
| WO | 2009145323 | 12/2009 |
| WO | 2010025303 A1 | 3/2010 |
| WO | 2011011781 A1 | 1/2011 |
| WO | 2012028620 A1 | 3/2012 |
| WO | 2013048558 A2 | 4/2013 |
| WO | 2013158145 A1 | 10/2013 |
| WO | 2014081977 | 5/2014 |
| WO | 2015048818 | 4/2015 |
| WO | 2015057747 | 4/2015 |
| WO | 2015063659 | 5/2015 |
| WO | 2015187641 | 12/2015 |
| WO | 2017147193 | 8/2017 |
| WO | 2017205515 | 11/2017 |
| WO | 2019051158 | 3/2019 |

OTHER PUBLICATIONS

Ahrens, M. et al. (Jan. 2001). 'Consensus Statement From a Conference for the Management of Patients With Urea Cycle Disorders.' Supp. Journal of Pediatrics 138(1 ):S1-S5.

Alfentanil Highlights of Prescribing information Dec. 2016 (Year: 2016); 19 pages.

Amara et al., Biochim. Biophys. Acta 1791: 983-990, 2009.

Ambrose, A.M. et al. (1933). 'Further Studies on the Detoxification of Phenylacetic Acid,' J. Bio. Chem. 101:669-675.

Amended Complaint, *Horizon Therapeutics, Inc.* v. *Lupin Ltd. and Lupin Pharmaceuticals Inc.* Filed in U.S. District Court for the District of New Jersey, Apr. 6, 2016, 10 pgs.

Ammonul Product Specification, Cangene Biopharma Inc. Feb. 2005.

Amodio, P., et al., "Detection of Minimal Hepatic Encephalopathy: Normalization and Optimization of the Psychometric Hepatic Encephalopathy Score. A Neuropsychological and Quantified EEG Study," J. Hepatol. 49:346-353 (2008).

Anda Notice Letter, Lupin Ltd. to Horizon T herapeutics, Inc.. Re: Notitication of invalidity, Unenforceability, and/or Noninfringement for U.S. Pat. No. 8,404,215 and 8,642,012 Pursuant to 505(j)(2)(B)(ii) and (iv) of the Federal Food, Drug, and Cosmetic Act, Sep. 4, 2015.

Anda Notice Letter, Lupin Ltd. to Horizon Therapeutics, Inc.. Re: Notification of Invalidity, Unenforceability, and/or Noninfringement for U.S. Pat. No. 9,095,559 Pursuant to 505(j)(2)(B)(ii) and (iv) of the Federal Food, Drug, and Cosmetic Act, Nov. 6, 2015, 30 pgs.

Anda Notice Letter, Lupin Ltd. to Horizon Therapeutics, Inc.. Re: Notification of Invalidity, Unenforceability, and/or Noninfringement for U.S. Pat. No. 9,254,278 Pursuant to 505(j)(2)(B)(ii) and (iv) of the Federal Food, Drug, and Cosmetic Act, Apr. 13, 2016, 42 pgs.

Anda Notice Letter, Par Pharmaceutical, Inc. To Horizon Therapeutics, LLC.. Re: Glycerol Phenylbutyrate oral liquid 1.1 gm/ml; U.S. Pat. No. 9,962,359 and Notice of Paragraph IV Certification Jul. 23, 2018, 20 pgs.

Anda Notice Letter, Par Pharmaceutical, Inc. to Hyperion Therapeutics, inc.. Re: Glycerol Phenylbutyrate 1.1 gm/ml oral liquid; U.S. Pat. No. 8,404,215 and 8,642,012 Notice of Paragraph IV Certification Mar. 12, 2014, 27 pgs.

Andersson et al., Biochim. Biophys. Acta 1302: 236-240, 1996.

Anonymous, "Application No. 20-645 Medical Review FDA", (Feb. 15, 2005), pp. 1-55, URL: http://www.accessdata.fda.gov/drugsatfda_docs/nda/2005/020645s000_MedR.pdf, (Mar. 22, 2016), XP055260195.

Bajaj, J. S., et al., 'Review Article: The Design of Clinical Trials in Hepatic Encephalopathy—An International Society for Hepatic Encephalopathy and Nitrogen Metabolism (ISHEN) Consensus Statement,' Aliment Pharmacol Ther. 33 (7):739-747 (2011).

Barsotti, 'Measurement of Ammonia in Blood', 138 J. Pediatrics, S11-S20 (2001).

Batshaw M.L. et al. (Jun. 10, 1982) 'Treatment of Inborn Errors of Urea Synthesis: Activation of Alternative Pathways of Waste Nitrogen Synthesis and Excretion,' N Engl J Med 306(23):1387-1392.

Batshaw, M. L. et. al., Alternative Pathway Therapy for Urea Cycle Disorder: Twenty Years Later, 138 J. Pediatrics S46 (2001).

Batshaw, M.L. (1984). 'Hyperammonemia,' in Current Problems in Pediatrics, Lockhart, J.D. ed.: Year Book Medical Publishers, pp. 2-69.

Batshaw, M.L. et al. (Aug. 1981) 'New Approaches to the Diagnosis and Treatment of Inborn Errors of Urea Synthesis,' Pediatrics 68(2):290-297.

Batshaw, M.L. et al. (Dec. 1980). 'Treatment of Hyperammonemic Coma Caused by Inborn Errors of Urea Synthesis,' J. Pediatr. 97(6):893-900.

Batshaw, M.L. et al., Treatment of Carbamyl Phosphate Synthetase Deficiency with Keto Analogues of Essential Amino Acids, 292 The New England J. Medicine, 1085-1090 (1975).

Berry et al., Mol. Gen. And Metab. 122: 46-53, 2017.

(56) References Cited

OTHER PUBLICATIONS

Berry et al., Poster titled "Pharmacokinetics of glycerol phenylbutyrate in pediatric patients 2 months to 2 years of age with urea cycle disorder" presented at American Society of Human Genetics Meeting, Oct. 17-21, 2017.

Berry SA et al., Glycerol phenylbutyrate treatment in children with urea cycle disorders: pooled analysis of short and long-term ammonia control and outcomes, Mol Genet Metab. May 2014;112(1):17-24.

Berry, G. T., et al., 'Long-Term Management of Patients with Urea Cycle Disorders,' J. Pediatrics (2001) 138:S56-S61.

Blei, A. T., et al., 'Hepatic Encephalopathy,' Am. J. Gastroenterol. 96(7): 1968-1976 (2001).

Boulieu, R. et al., "Pharmacokinetics of Midazolam and its main metabolite 1-hydroxymidazolam in intensive care patients", Eur J Drug Metab Pharmacokinet., 23(2):255-8, (1998).

Brahe, C., et al., (2005) 'Phenylbutyrate Increases SMN Gene Expression in Spinal Muscular Atrophy Patients,' Eur J Hum Genet 13:256-259.

Brendan Lee et al, 'Blood ammonia and glutamine as predictors of hyperammonemic crises in patients with urea cycle disorder', Genetics in Medicine, US, (Dec. 11, 2014), vol. 17, No. 7, doi:10.1038/gim.2014.148, ISSN 1098-3600, pp. 561-568, XP055260189.

Brunetti-Pierri, N., et al., (2011) Phenylbutyrate Therapy for Maple Syrup Urine Disease, Hum Mol Genet 20(4):631-640.

Brusilow et al., Metabolism, vol. 42, No. 10 Oct. 1993, pp. 1336-1339, 'Restoration of Nitrogen Homeostasis in a Man with Ornithine Transcarbamylase Deficiency'.

Brusilow, S. W., 'Phenylacetylglutamine May Replace Urea as a Vehicle for Waste Nitrogen Excretion,' Ped. Res. 29(2):147-150(1991).

Brusilow, S.W. (1995). 'Urea Cycle Disorders: Clinical Paradigm of Hyperammonemic Enecphalopathy,' Chapter 12 in Progress in Liver Diseases pp: 293-309.

Brusilow, S.w. (Jun. 21,1984). 'Treatment of Episodic Hyperammonemia in Children With Inborn Errors of Urea Synthesis,' N. Engl. J. Med. 310(25):1630-1634.

Brusilow, S.W. et al. (1995). 'Urea Cycle Enzymes,' Chapter 32 in The Metabolic and Molecular bases of Inherited Diseases, Scriver, C.R. et al. eds., McGraw-Hill, Inc. New York, pp. 1187-1232.

Brusilow, S.W., 'Protocols for Management of Intercurrent Hyperammonemia in Patients with Urea Cycle Disorders', FDA Application to Market a New Drug for Human Use or an Antibiotic Drug for Human Use, Fourteen pages (Amendment Dated Jul. 25,1994).

Brusilow, S.W., et al. (Sep. 1, 1979) 'New Pathways of Nitrogen Excretion in Inborn Errors of Urea Synthesis,' Lancet 2(8140):452-454.

Brusilow, S.W., et al. (Feb. 8, 1980) 'Amino Acid Acylation: A Mechanism of Nitrogen Excretion in Inborn Errors of Urea Synthesis,' Science 207:659-661.

Brusilow, S.W., et al. (1991) 'Treatment of Urea Cycle Disorders,' Chapter 5 in Treatment of Genetic Diseases, Desnik, R.J. et al. eds, Churchill Livingstone, New York, New York, pp. 79-94.

Brusilow, S.W., et al. (1996) 'Urea Cycle Disorders: Diagnosis, Pathophysiology, and Therapy,' Adv Pediatr 43:127-170.

Burlina, A.B. et al., 'Long- Term Treatment with Sodium Phenylbutyrate in Ornithine Transcarbamylase-Deficient Patients', 72 Molecular Genetics and Metabolism 351-355 (2001).

Calloway, D.H. et al. (1971) 'Sweat and Miscellaneous Nitrogen Losses in Human Balance Studies,' J Nutrition 101:775-786.

Calloway, D.H. et al. (1971). 'Variation in Endogenous Nitrogen Excretion and Dietary Nitrogen Utilization as Determinants of Human Protein Requirements,' J. Nutrition 101:205-216.

Camacho, L.H. et al., Phase I Dose Escalation Clinical Trial of Phenylbutyrate Sodium Administered Twice Daily to Patients With Advanced Solid Tumors, 25 Invest. New Drugs 131-138 (2007, e-pub. Oct. 20, 2006).

Carducci, M., Phenylbutyrate Induces Apoptosis in Human Prostate Cancer and Is More Potent Than Phenylacetate, 2 Clinical Cancer Research 379-387 (1996).

Carducci, M.A. et al., A Phase I Clinical and Pharmacological Evaluation of Sodium Phenylbutyrate on an 120-h Infusion Schedule, 7 Clin. Cancer Res. 3047-3055 (2001).

Center for Drug Evaluation and Research, Clinical Pharmacology and Biopharmaceutics Review for New Drug Application No. 20-645 (Ammonul) (2005), 34 pgs.

Center for Drug Evaluation and Research, Labeling for New Drug Application No. 20-645 (Ammonul.RTM.) (2005).

Center for Drug Evaluation and Research, Medical Review for New Drug Application No. 20-645 (Ammonul) (2005), 55 pgs.

Chang J.-G., et al., 'Treatment of Spinal Muscular Atrophy by Sodium Butyrate,' PNAS USA (2001) 98(17):9808-9813.

Chang, C.-S.; Wu, P.-L. 'Synthesis of triglycerides of phenybutyric acid by lipase', J. Molecular Catalysis B: Enzymatic 61, 117-122 (2009).

Chang, C.-S.; Wu, P.-L. 'Synthesis of triglycerides of phenylalkanoic acids by lipase-catalyzed esterification in a solvent-free system', J. Biotech. 127, 694-702 (2007).

Chemical Abstracts, vol. 112, No. 25, Jun. 18, 1990, (Columbus, Ohio, USA), p. 270, Abstract No. 231744t, Walsh J.P., "SN-1,2-Diacylglycerol Kinase of *Escherichia coli*. Diacylglycerol Analogs Define Specificity and Mechanism"; & Journal of Biological Chemistry, 1990, 265(8), (Eng).

Chen et al., 'Tributyrin: A Prodrug of Butyric Acid for Potential Clinical Applicaitn in Differentiation Therapy', Cancer Res., 54:3494-3499(1994).

Chung, Y.L., et al., (2000) "A Novel Approach for Nasopharyngeal Carcinoma Treatment Uese Phenylbutyrate as a Protein Kinase C Modulator: Implications for Radiosensitization and EBV-Targeted Therapy," Clin Cancer Res 6:1452-1458.

Clay, A. et. al, Hyperammonemia in the ICU, 132 Chest 1368-1378 (2007).

ClinicalTrials.Gov/Archive View of NCT00551200 on Dec. 11, 2007 'Dose-Escalation Safety Study of Glyceryl Tri (4-Phenylbutyrate)(GT4P) to Treat Urea Cycle Disorders' [accessed Oct. 5, 2009], 4 pages.

Collins, A.F. et al., Oral Sodium Phenylbutyrate Therapy in Homozygous Beta Thalassemia: a Clinical Trial, 85 Blood 43-49 (1995).

Combined Search and Examination Report dated Oct. 9, 2009 for Great Britain Patent Application No. GB0915545.8, filed on Aug. 27, 2009, eight pages.

Combined Search and Examination Report dated Sep. 9, 2010, for Great Britian Patent Application No. 1013468.2, filed on Aug. 27, 2009, six pages.

Complaint for Patent Infringement, *Horizon Therapeutics, Inc.* v. *Lupin Ltd. and Lupin Pharmaceuticals Inc.* Filed in U.S. District Court for the District of New Jersey, Oct. 19, 2015, 104 pgs.

Complaint for Patent Infringement, *Horizon Therapeutics, LLC* v. *Par Pharmaceutical, Inc. and Par Pharmaceutical Companies, Inc.*, Filed in U.S. District Court for the District of Delaware, Aug. 10, 2018, 15 pgs.

Complaint for Patent Infringement, *Hyperion Therapeutics, Inc.* v. *Par Pharmaceuticals, Inc.* Filed in U.S. District Court for the Eastern District of Texas, Apr. 23, 2014, 14 pgs.

Complaint', *Horizon Therapeutics, Inc.* v. *Lupin Ltd. et al.*; U.S. District Court for the District of New Jersey; Civ. Action No. 1:16-cv-00438-RBK-JS; Filed Jul. 21, 2016.

Complaint', *Horizon Therapeutics, Inc.* v. *Par Pharmaceutical, Inc.*; U.S. District Court for the District of New Jersey; Civ. Action No. 1:16-cv-03910-RBK-JS; Filed Jun. 30, 2016.

Complaint', *Horizon Therapeutics, Inc.* v. *Par Pharmaceutical, Inc.*; U.S. District Court for the District of New Jersey; Civ. Action No. 2:17-cv-05901-KM-MAH; Filed Aug. 8, 2017.

Comte, B. et al. (2002, e-pub. May 7, 2002). 'Identification of Phenylbutyrylglutamine, A New Metabolite of Phenylbutyrate Metabolism in Humans,' Journal of Mass Spectrometry 37(6):581-590.

Conn, H. O., et al., "Liver Physiology and Disease: Comparison of Lactulose and Neomycin in the Treatment of Chronic Portal-Systemic Encephalopathy. A Double Blind Controlled Trial," Gastroenterology 72(4):573-583 (1977).

Cordoba, J., "New assessment of hepatic encephalopathy"., Journal of Hepatology, (2011), vol. 54, p. 1030, 1032, 1038, XP028192163.

(56) References Cited

OTHER PUBLICATIONS

Cudkowicz (2009) Phase 2 Study of Sodium Phenylbutyrate in ALS,—Amyotrophic Lateral Sclerosis 10:99-106.
Darmaun, D. et al., 'Phenylbutyrate-Induced Glutamine Depletion in Humans: Effect on Leucine Metabolism', 5 Am. J. of Physiology: Endocrinology and Metabolism E801 (1998).
Darzens, G. et al.: 'Preparation de quelques glycerides phenylaliphatiques et leur reduction en alcools . . . ', Comptes Rendus Hebdomadaires Des Seances De L'Academie Des Sciences., vol. 205, Oct. 18, 1937, pp. 682-684.
Deferrari, G. et al. (1981). 'Brain Metabolism of Amino Acids and Ammonia in Patients with Chronic Renal Insufficiency,' Kidney International 20:505-510.
Diaz G.A.et al, 'Ammonia (NH3) control and improved neurocognitive outcome among urea cycle disorder (UCD) patients treated with glycerol phenylbutyrate (GPB).' Mol. Genet. Metab. 2012,105, 311, SIMD Abstract 24.
Diaz, G. A., et aL., Ammonia control and Neurocognitive Outcome Among urea Cycle Disorder Patients Treated with Glycerol Phenylbutyrate, Hepatology 57(6):2171-2179 (2013).
Diaz, G.A., et al., 'Phase 3 Blinded, Randomized, Crossover Comparison of Sodium Phenylbutyrate (NaPBA) and Glycerol Phenylbutyrate (GPB): Ammonia (NH3) Control in Adults with Urea Cycle Disorders (UCDs),' Mol. Genet. Metab. 102:276, Society of Inherited Metabolic Disease (SMID) Abstract, (2011).
Dixon, M. A. and Leonard, J.V., Intercurrent Illness in Inborn Errors of Intermediary Metabolism, 67 Archives of Disease in Childhood, 1387-1391 (1992).
Doi, et al., "Development of an Azanoradamantane-Type Nitroxyl Radical Catalyst for Class-Selective Oxidation of Alcohols," J Org Chem 80 (1), 401-413. Dec. 16, 2014.
Dover, G. et al, Induction of Fetal Hemoglobin Production in Subjects with Sickle Cell Anemia by Oral Sodium Phenylbutyrate, 84(1) Blood 339-343.
DSM Method of Analysis: Assay of Impurities in PERU 1 by HPLC (Oct. 21, 2011).
Endo, F. et al., Clinical Manifestations of Inborn Errors of the Urea Cycle and Related Metabolic Disorders During Childhood, 134 J. Nutrition 1605S (2004).
Enns et al., 'Survival after Treatment with Phenylacetate and Benzoate for Urea-Cycle Disorders', N Engl J Med., vol. 356, No. 22, (May 31, 2007), pp. 2282 -2292, URL: http://www.nejm.org, XP055148817.
Enns GM (Author),Edited by Jess G. Thoene, Alternative waste nitrogen disposal agents for urea cycle disorders (Chapter 10), Small Molecule Therapy for Genetic Disease, Cambridge University Press., 2010, pp. 135-152.
European Medicines Agency, Annex I: Summary of Product Characteristics for Ammonaps, 1-33.
European Medicines Agency, European Public Assessment Report: Summary for the Public for Ammonaps (2009), 2 pgs.
European Medicines Agency, Scientific Discussion for Ammonaps (2005), 12 pgs.
European Medicines Agency, Scientific Discussion for Carbaglu (2004), 19 pgs.
European Patent Office, Extended European Search Report for EP09739263 completed Nov. 2, 2011, 6 pgs.
European Patent Office, International Search Report and Written Opinion for PCT/ US2009/055256 completed Dec. 18, 2009 and dated Dec. 30, 2009, 13 pgs.
Examination Report for British Patent Application No. GB0915545.8 dated Oct. 27, 2010.
Examination Report for British Patent Application No. GB1013468.2 dated Oct. 28, 2011, 2 pgs.
Examination Report dated Feb. 5, 2010, for United Kingdom Patent Application No. GB0915545.8, filed on Aug. 27, 2009, two pages.
Examination Report dted May 11, 2010, for United Kingdom Patent Application No. GB0915545.8 filed on Aug. 27, 2009, one page.
Eydoux et al., J. Lipid. Res. 48: 1539-1549, 2007.
FDA Label for Ammonul, sixteen pages {Feb. 2005).
FDA Label for Carbagiu, seven pages. (Mar. 2010).
FDA. 'Buphenyl (Sodium Phenylbutyrate) Label' nine pages (Aug. 2003).
FDA. (Jul. 2007). 'Label for Buphenyl,' 6 pages.
Feillet, F. and Leonard, J.V., Alternative Pathway Therapy for Urea Cycle Disorders, 21 J. Inher. Metab. Dis. 101-111 (1998).
Feoli-Fonseca, M. L., Sodium Benzoate Therapy in Children with Inborn Errors of Urea Synthesis: Effect on Carnitine Metabolism and Ammonia Nitrogen Removal, 57 Biochemical and Molecular Medicine 31-36 (1996).
Ferenci, P., et al., 'Hepatic EncephalopathyDefinition, Nomenclature, Diagnosis, and Quantification: Final Report of the Working Party at the 11th World Congresses of Gastroenterology, Vienna, 1998,' Hepatology 35:716-721 (2002).
Fernandes, Saudubray, Berghe (editors), 'Inborn Metabolic Diseases Diagnosis and Treatment', 219-222 (3d ed. 2000).
Fey, et al., "Silica-Supported TEMPO Catalysts: Synthesis and Application in the Anelli Oxidation of Alcohols," J. Org. Chem., 2001, 66 (24), pp. 8154-8159.
Gargosky, S. 'Improved Survival of Neonates Following Administration of Ammonul (Sodium Phenyl acetate & Sodium Benzoate) 10% 110% Injection', Ssiem Poster, six pages (Aug. 2, 2005).
Gargosky, S. et al., 'Results of a Twenty-two Year Clinical Irial: Acute, Adjunctive Pharmacological Treatment of Hyperammonemic Episodes in Patients with Deficiencies in Enzymes of the Urea Cycle', poster, Ucyclyd Pharma, Inc., one page (Oct. 14, 2005).
Gargosky, s., High Ammonia Levels Are Associated with Increased Mortality and Coma , Ucyclyd Pharma, Inc., one page (2006).
Geraghty, M.T. and Brusilow, S.W., Disorders of the Urea Cycle, in Liver Disease in Children 827-842 (F.J. Suchy et al., eds. 2001).
Ghabril, M. et al., Glycerol Phenylbutyrate (GPB) Administration in Patients with Cirrhosis and Episodic Hepatic Encephalopathy {HE), accepted for presentation at Digestive Disease Week (2012).
Ghabril, M., et al., 'Glycerol Phenylbutyrate in Patients With Cirrhosis and Episodic Hepatic Encephalopathy: A Pilot Study of Safety and Effect on Venous Ammonia Concentration,' Clinical Pharmacology in Drug Development 2 (3):278-284 (2013).
Gilbert, J. et al., A Phase I Dose Escalation and Bioavailability Study of Oral Sodium Phenylbutyrate in Patients with Refractory Solid Tumor Malignancies, 7 Clin. Cancer Research 2292-2300 (2001).
Gore, S. et al., 'Impact or the Putative Differentiating Agent sodium Phenylbutyrate on Myelodysplastic Syndromes and Acute Myeloid Leukemia', 7 Clin. Cancer Res. 2330 (2001).
Gropman, A. (2010) "Brain Imaging in Urea Cycle Disorders," Mol Genet Metab 100:S20-S30.
Gropman, A.L. et al. (2008) '1H MRS Identifies Symptomatic and Asymptomatic Subjects With Partial Ornithine Transcarbamylase Deficiency,' Mol. Genet. Metab. 95(1-2):21-30 (Sep.-Oct. 2008, e-pub. Jul. 26, 2008).
Gropman, A.L. et al., Neurological Implications of Urea Cycle Disorders, 30 J. Inherit Metab Dis. 865-879 (2007).
Gropman, A.L., et al., (2008) '1H MRS Allows Brain Phenotype Differentiation in Sisters with Late Onset Ornithine Transcarbamylase Deficiency (OTCD) and Discordant Clinical Presentations,' Mol Genet Metab 94(1):52-60.
Guidance for Industry, Jul. 2005 to show proper dosage calculation. (Year 2005).
Häberle J etal., Suggested guidelines for the diagnosis and management of urea cycle disorders, Orphanet J Rare Dis. May 29, 2012;7:32.
Hassanein, T. I., et al., "Introduction to the Hepatic Encephalopathy Scoring Algorithm (HESA)," Dig. Dis. Sci. 53:529-538 (2008).
Hassanein, T. I., et al., "Randomized Controlled Study of Extracorporeal Albumin Dialysis for Hepatic Encephalopathy in Advanced Cirrhosis," Hepatology 46:1853-1862 (2007).
Hassanein, T., et al., 'Performance of the Hepatic Encephalopathy Scoring Algorithm in a Clinical Trial of Patients With Cirrhosis and Severe Hepatic Encephalopathy,' Am. J. Gastroenterol. 104:1392-1400 (2009).
Helsinn Advanced Synthesis, Analytical Method, 03-GLIO Related Substances (Sep. 2011).

(56) References Cited

OTHER PUBLICATIONS

Helsinn Summary Report of Analytical Methods Validation (May 23, 2011).
Hines, P., et al., (2008) 'Pulsed-Dosing with Oral Sodium Phenylbutyrate Increases Hemoglobin F in a Patient with Sickle Cell Anemia,' Pediatr Blood Cancer 50:357-359.
Hogarth, P., et al., (2007) 'Sodium Phenylbutyrate in Huntington's Disease: A Dose-Finding Study,' Mov Disord 22(13):1962-1964.
Honda, S. et al., Successful Treatment of Severe Hyperammonemia Using Sodium Phenylacetate Power Prepared in Hospital Pharmacy, 25 Biol. Pharm. Bull. 1244-1246 (2002).
Huang, H.H., et al., (2012) "Cannabinoid Receptor 2 Agonist Ameliorates Mesenteric Angiogenesis and Portosystemic Collaterals in Cirrhotic Rats," Hepatology 56:248-258.
Hyperion Therapeutics. 'Hyperion Therapeutics Announces Enrollment of First Patient in Phase 1/2 Clinical Trial of GT4P in Patients with Urea Cycle Disorders' Announcement, 1 page (Oct. 23, 2007).
Hyperion Therapeutics. 'Hyperion Therapeutics Announces Results for Phase II Study in Urea Cycle Disorders,' located at <http://www.hyperiontx.com/press/release/pr1238518388,> last visited on Apr. 27, 2011, three pages (Mar. 30, 2009).
Hyperion Therapeutics. "Hyperion Therapeutics Announces Presentation of Long Term Data on Ammonia Control in Pediatric Patients Treated with Ravicti® at the 12th International Congress of Inborn Errors of Metabolism and the Urea Cycle Disorder Satellite Symposium", Press Release, Sep. 3, 2013.
Hyperion Therapeutics. (Jun. 2, 2009.) Hyperion Therapeutics Announces Results of Phase I Study in Patients with Liver Cirrhosis, located at <http://www.hyperiontx.com/press/release/pr_1243891161>, last visited on Apr. 27, 2011, three pages.
International Application No. PCT/US1996/000940, International Search Report, dated Aug. 15, 1996, 1 page.
International Application No. PCT/US2009/030362, International Preliminary Report on Patentability, dated Mar. 1, 2011, filed on Jan. 7, 2009, seven pages.
International Application No. PCT/US2012/028620, International Preliminary Report on Patentability (Ch II), completed Aug. 22, 2013 and dated Sep. 4, 2013, 16 pgs.
International Application No. PCT/US2014/058489, International Preliminary Report on Patentability (Ch I), dated Apr. 5, 2016. 7 pages.
International Application No. PCT/US2014/060543, International Preliminary Report on Patentability (Ch I), dated Apr. 19, 2016 8 pages.
International Application No. PCT/US2015/033700, International Preliminary Report on Patentability (Ch I), dated. Dec. 6, 2016, 8 pages.
International Application No. PCT/US2015/033700, International Search Report and Written Opinion dated Aug. 19, 2015, 10 pgs.
International Preliminary Report on Patentability dated Mar. 1, 2011, for PCT Application No. PCT/US2009/055256, filed on Aug. 27, 2009, six pages.
IPR2015-01117, Inter Partes Review of U.S. Pat. No. 8,642,012, Petition, 186 pgs, Apr. 29, 2015.
IPR2015-01117, Inter partes review of U.S. Pat. No. 8,642,012, Final written decision 35 U.S.C. § 318 and 37 C.F.R. § 42.73.
IPR2015-01127, Inter Partes Review of U.S. Pat. No. 8,404,215 Petition Apr. 29,2015.
IPR2015-01127, Inter partes review of U.S. Pat. No. 8,404,215, Final written decision 35 U.S.C. § 318 and 37 C.F.R. § 42.73.
IPR2016-00283, Inter partes review of U.S. Pat. No. 8,642,012, Final written decision 35 U.S.C. § 318 and 37 C.F.R. § 42.73.
IPR2016-00283, Inter partes review of U.S. Pat. No. 8,642,012, Petition, pursuant to §§ 35 U.S.C. 311-319 and 37 C.F.R. § 42, Dec. 4, 2015.
IPR2016-00284, Inter partes review of U.S. Pat. No. 8,404,215, Final written decision 35 U.S.C. § 318 and 37 C.F.R. § 42.73.
IPR2016-00284, Inter partes review of U.S. Pat. No. 8,404,215, Petition, pursuant to §§ 35 U.S.C. 311-319 and 37 C.F.R. § 42, Dec. 4, 2015.
IPR2016-00829, Inter partes review of U.S. Pat. No. 9,095,559, Patent owner response.
IPR2016-00829, Inter partes review of U.S. Pat. No. 9,095,559, Petition, pursuant to §§ 35 U.S.C. 311-319 and 37 C.F.R. § 42, Apr. 1, 2016.
IPR2017-01159, Inter partes review of US patent no. 9 9,254,278, Petition, pursuant to §§ 35 U.S.C. 311-319 and 37 C.F.R. § 42.
IPR2017-01159, Inter partes review of US patent no. 9 9,254,278, Preliminary Patent Owner Response.
IPR2017-01160, Inter partes review of U.S. Pat. No. 9,326,966, Petition, pursuant to §§ 35 U.S.C. 311-319 and 37 C.F.R. § 42.
IPR2017-01160, Inter partes review of U.S. Pat. No. 9,326,966, Preliminary Patent Owner Response.
IPR2017-01767, Inter partes review of U.S. Pat. No. 9,254,278, Petition, pursuant to §§ 35 U.S.C. 311-319 and 37 C.F.R. § 42.
IPR2017-01768, Inter partes review of U.S. Pat. No. 9,095,559, Petition, pursuant to §§ 35 U.S.C. 311-319 and 37 C.F.R. § 42.
IPR2017-01769, Inter partes review of U.S. Pat. No. 9,326,966, Petition, pursuant to §§ 35 U.S.C. 311-319 and 37 C.F.R. § 42.
IPR2018-01550, Inter partes review of U.S. Pat. No. 9,561,197, Petition, pursuant to § 35 U.S.C. 311-319,37, and 42 C.F.R., dated Aug. 16, 2018, 60 pages.
James, M.O. et al. (1972). 'The Conjugation of Phenylacetic Acid in Man, Sub-Human Primates and Some Other Non-Primates Species,' Proc. R. Soc. London 182:25-35.
John, B.A., et al., 'The Disposition of HPN-100, A Novel Pharmaceutical Under Development for Potential Treatment of Hyperammonemia, in Cynomolgus Monkeys', ADMG 2009 ADME, poster, two pages (Mar. 2009).
John, Ba et al. (Mar. 2009). 'The Disposition of HPN-100, A Novel Pharmaceutical Under Development for Potential Treatment of Hyperammonemia, in Cynomologus Monkeys,' abstract presented at ACMG 2009, one page.
Jon P. R. Monteleone et al, 'Population Pharmacokinetic Modeling and Dosing Simulations of Nitrogen-Scavenging Compounds: Disposition of Glycerol Phenylbutyrate and Sodium Phenylbutyrate in Adult and Pediatric Patients with Urea Cycle Disorders', Journal of Clinical Pharmacology., US, (Jun. 15, 2013), vol. 53, No. 7, doi:10.1002/jcph.92, ISSN 0091-2700, pp. 699-710, XP055244763.
Kasumov, T. et al. (2004). 'New Secondary Metabolites of Phenylbutyrate in Humans and Rats,' Drug Metabolism and Disposition 32(1 ):10-19.
Khungar V et al, 'Management of Overt Hepatic Encephalopathy', Clinics in Liver Disease 2012 W.B. Saunders USA, (Feb. 2012), vol. 16, No. 1, ISSN 1089-3261, pp. 73-89, XP008179943.
Kleppe, S. et al., 'Urea Cycle Disorders', 5 Current Treatment Options in Neurology 309-319 (2003).
Koya, Toshinari et al., Poster Session, Liver P-397, A study of administration of granular preparations of branched chain amino acids during transcatheter arterial chemoembolisation for hepatocellular carcinoma, Department of Gastrointestinal Medicine, Anjo Kosei Hospital, 2017, p. A775.
Kubota, K. and Ishizaki, T., Dose-Dependent Pharmacokinetics of Benzoic Acid Following Oral Administration of Sodium Benzoate to Humans, 41 Eur. J. Clin. Pharmacol. 363-368 (1991).
Lea et al., 'Butyramide and Monobutyrin: Growth Inhibitory and Differentiating Agents', Anticancer Res., 13: 145-150 (1993).
Lee, B. and Goss, J., Long-Term Correction of Urea Cycle Disorders, 138 J. Pediatrics S62-S71 (2001).
Lee, B. et al. (2009) 'Dosing and Therapeutic Monitoring of Ammona Scavenging Drugs and Urinary Phenylacetylglutamine (PAGN) as a Biomarker: Lessons From a Phase 2 Comparison of a Novel Ammonia Scavenging Agent with Sodium Phenylbutyrate (NAPBA),' "abstract" presented at ICIEM 2009, San Diego, CA, poster, one page.
Lee, B. et al. (2009) 'Phase 2 Study of a Novel Ammonia Scavenging Agent in Adults With Urea Cycle Disorders (UCDs),' abstract presented at ACMG 2009, one page.
Lee, B. et al. (Aug. 2008). 'Preliminary Data on Adult Patients with Urea Cycle Disorders (UCD) in an Open-Label, Swirch-Over, Dose Escalation Study Comparing a New Ammonia Scavenger, Glyceryl

(56) References Cited

OTHER PUBLICATIONS

Tri (4-Phenylbutyrate) [HPN-100], to Buphenyl (Sodium Phenylbutyrate [PBA])', abstract presented at SSSIEM 2008, Lisbon, Portugal, one page.
Lee, B. et al., "Phase 2 Study of a Novel Ammonia Scavenging Agent in Adults with Urea Cycle Disorders (UCDs)", presented at ACMG 2009, seventeen pages (Mar. 2009).
Lee, B. et al., "Preliminary Data on Adult Patients with Urea Cycle Disorders (UCD) in an Open-Label, Switch-Over, Dose Escalation Study Comparing a New Ammonia Scavenger, Glyceryl Tri (4-Phenylbutyrate) [HPN-100], to Buphenyl® (Sodium Phenylbutyrate [PBA])", presented at SSIEM 2008, Lisbon, Portugal, Poster, one page (Sep. 2008).
Lee, B. et al., Considerations in the Difficult-to-Manage Urea Cycle Disorder Patient, 21 Crit. Care Clin. S19-S25 (2005).
Lee, B., et al., 'Optimizing Ammonia (NH3) Control in Urea Cycle Disorder (UCD) Patients: A Predictive Model,' Oral Abstract Platform Presentations, Biochemical Genetics, Phoenix, AZ, Mar. 22, 2013, 2 pgs.
Lee, B., et al., 'Phase 2 Comparison of a Novel Ammonia Scavenging Agent with Sodium Phenylbutyrate in Patients with Urea Cycle Disorders: Safety, Pharmacokinetics and Ammonia Control,' Mol. Genet. Metab. 100(3):221-228 (2010).
Lee, B., et al., "Preliminary Data on Adult Patients with Urea Cycle Disorders (UCD) in an Open-Label, Switch-Over, Dose-Escalation Study Comparing a New Ammonia Scavenger, Glyceryl Tri(4-Phenylbutyrate) (HPN-100), to Buphenyl (Sodium Phenylbutyrate [PBA])", 31 J. Inherit. Metab. Dis. 91 (2008).
Leonard, J.V., Urea Cycle Disorders, 7 Semin. Nenatol. 27-35 (2002).
Levin, B. et al. "Hyperammonaemia: A Variant Type of Deficiency of Ornithinine Transcarbamylase." Arch. Dis. Childhd. 1969, 44, 162-169.
Lewis, H.B. (1914). 'Studies in the Synthesis of Hippuric Acid in the Animal Organism. II. The Synthesis and Rate of Elimination of Hippuric Acid After Benzoate Ingestion in Man,' J. Biol. Chem. 18:225-231.
Liang, K.Y., et al., 'Longitudinal Data Analysis Using Generalized Linear Models,' Biometrika 73(1):13-22 (1986).
Lichter-Konecki, U. et al., "Ammonia Control in Children with Urea Cycle Disorders (UCDs); Phase 2 Comparison of Sodium Phenylbutyrate and Glycerol Phenylbutyrate", Mol Genet Mateb., 103(4):323-9, (2011).
Lindquist and Hernell, Curr Opin Clin Nutr Metab Care 13: 314-320, 2010.
Lizardi-Cervera, J. et al, 'Hepatic Encephalopathy: A Review', 2 Annals of Hepatology 122-120 (2003).
MacArthur, R. B., et al., 'Pharmacokinetics of sodium phenylacetate and soium benzoate following intravenous administrtion as both a bolus and continuous infusion to healthy adult volunteers.' Mol Genet Metab 81 :(1 ):S67-S73 (2004).
Maestri NE, et al., Prospective treatment of urea cycle disorders. J Paediatr 1991 ;119:923-928.
Maestri, N.E. et al., 'Plasma Glutamine Concentration: A Guide in the Management of Urea Cycle Disorders', 121 J. Pediatrics 259 (1992).
Maestri, N.E., et al., Long-Term Survival of Patients with Argininosuccinate Synthetase Deficiency, 127 J. Pediatrics 929-935 (1993).
Maestri, N.E., Long-Term Treatment of Girls with Ornithine Transcarbamylase Deficiency, 355 N. Engl. J. Med. 855-859 (1996).
Majeed, K., Hyperammonemia, eMedicine.com (Dec. 2001), 12 pgs.
Mansour, A. et al. (Oct. 1997). 'Abdominal Operations in Patients with Cirrhosis: Still a Major Surgical Challenge,' Surgery 122(4):730-735. (Abstract Only.).
Marini, J.C. et al., Phenylbutyrate Improves Nitrogen Disposal via an Alternative Pathway without Eliciting an Increase in Protein Breakdown and Catabolism in Control and Ornithine Transcarbamylase-Deficient Patients, 93 Am. J. Clin. Nutr. 1248-1254 (2011).
Mas et al., Biochem J. 289: 609-615, 1993.
Mas et al., Methods Enzymol. 284: 340-353, 1997.
Matsuda, I., Hyperammonemia in Pediatric Clinics: A Review of Ornithine Transcarbamylase Deficiency (OTCD) Based on our Case Studies, 47 JMAJ 160-165 (2004).
McGuire, B. et al. (2009) 'Pharmacokinetic (PK) and Safety Analyses of a Novel Ammonia-Reducing Agent in Healthy Adults and Patients with Cirrhosis,' abstract presented at DDW, two pages.
McGuire, B. et al. (2009) 'Pharmacokinetic (PK) and Safety Analyses of a Novel Ammonia-Reducing Agent in Healthy Adults and Patients with Cirrhosis,' Hyperion Therapeutics, poster, one page.
McGuire, B. et al., "Pharmacology and Safety of Glycerol Phenylbutyrate in Healthy Adults and Adults with Cirrhosis", Hepatology, 51(6):2077-85, (2010).
McGuire, B. et al., 'Pharmacokinetic <PK) Safety Study of Sodium Phenylacetate and Sodium Benzoate Administered to Subjects with Hepatic Impairment', abstract of the 13th International Symposium, Abano (Padova), Italy, Apr. 28-May 1, 2008, two pages (Apr. 2008).
McGuire, B. et al., "Pharmacokinetic Safety Study of Sodium Phenylacetate and Sodium Benzoate Administered to Subjects With Hepatic Impairments", 28 Liver International 743 (2008) (Abstract Only), 1 page.
McQuade, P.S., Analysis and the Effects of Some Drugs on the Metabolism of Phenylethylamine and Phenylacetic Acid, 8 Neuropsychopharmacol. Bio. Psychiat.607-614 (1984).
MedCalc: Body Surface Area Calculator, BSA of 21.65 Kg and 98.32 cm is 0.769 m2 using the Mostellar method, 2 pages. (Year: 2010).
MedCalc: Body Surface Area Calculator, BSA of 41.79 Kg and 133.66 cm is 1.246 m2 using the Mostellar method, 2 pages. (Year: 2010).
MedCalc: Body Surface Area Calculator, BSA of 61.93 Kg and 169 cm is 1.705 m2 using the Mostellar method, 2 pages. (Year: 2010).
Mercuri, E, et al, (2004) 'Pilot Trial of Phenylbutyrate in Spinal Muscular Atrophy,' Neuromuscul Disord 14:130-135.
Mizutani, N. et al., Hyperargininemia: Clinical Course and Treatment with Sodium Benzoate and Phenylacetic Acid, 5 Brain and Development 555-563 (1983).
Mokhtarani et al., (2012) 'Urinary phenylacetylglutamine appears to be a more useful marker than metabolite blood levels for therapeutic monitoring of phenylacetic acid (PAA) prodrugs.' Mol Genet Metab 105, 341-342, SIMD Abstract 78.
Mokhtarani, M, et al, (2012) 'Elevated Phenylacetic Acid (PAA) Levels Appear Linked to Neurological Adverse Events in Healthy Adults But Not in Urea Cycle Disorder (UCD) Patients,' Mol Genet Metab 105:342.
Mokhtarani, M., et al., 'Elevated Phenylacetic Acid Levels do not Correlate with Adverse Events in Patients with Urea Cycle Disorders or Hepatic Encephalopathy and Can Be Predicted Based on the Plasma PAA to PAGN Ratio,' Mol. Genet. Metab. 110(4):446-53 (2013).
Mokhtarani, M., et al., 'Urinary Phenylacetylglutamine as Dosing Biomarker for Patients with Urea Cycle Disorders,' Mol. Genet. Metab. 107(3):308-314 (2012).
Moldave, K, et al, (1957) 'Synthesis of Phenylacetylglutamine by Human Tissue,' J. Biol. Chem. 229:463-476.
Monteleone, JPR, et al., (2012) 'Population pk Analysis of Glycerol Phenylbutyrate (GPB) and Sodium Phenylbutyrate(NAPBA) in Adult and Pediatric Patients with Urea Cycle Discarders,' Mol Genet Metab 105:343-344.
Munoz, S. J, 'Hepatic Encephalopathy,' Med. Clin. N. Am. 92:795-812 (2008).
Nagazumi Atsushi et al., Use experience of Monilac for hepatic encephalopathy, Journal of New Remedies & Clinics, vol. 24, No. 8, Aug. 1975, pp. (1271-1274) 41-44.
Nassogne, M.C., Urea Cycle Defects: Management and Outcome, 28 J. Inherit. Metab. Dis. 407 (2005), 407-414.
National Center for Biotechnology Information. PubChem Compound Database; CID=10482134, https://pubchem.ncbi.nlm.nih.gov/compound/10482134 (accessed Jun. 8, 2018; create date: Oct. 25, 2006). (Year: 2006).
NCT00947297, Clinical Trial.gov archive, May 3, 2011.

(56) References Cited

OTHER PUBLICATIONS

NCT01347073 Clinical Trial.gov archive, May 3, 2011, Study of the safety, Pharmacokinetics and Efficacy of HPN-100, in Pediatric Subjects with Urea Cycle Dosorders (UCDs) 2011, 8 pages.

Newmark et al., 'Butyrate and Phenylacetate as Differentiating Agents: Practical Problems and Opportunities', Jour. of Cell. Biochem., Supplement 22: 247-253(1995).

Ong, J. P., et al., (2003) 'Correlation Between Ammonia Levels and the Severity of Hepatic Encephalopathy,' Am. J. Med. 114:188-193.

Ortiz, M., et al., "Development of a Clinical Hepatic Encephalopathy Staging Scale," Aliment Pharmacol Ther 26:859-867 (2007).

Par Pharmaceutical, Inc.s Initial Invalidity Contentions and Non-Infringement Contentions for U.S. Pat. No. 8,404,215 and 8,642,012, Nov. 13, 2014, 93. Pgs.

Parsons-Smith, B. G., et al., "The Electroencephalograph in Liver Disease," Lancet 273:867-871 (1957).

Peeters, M. et al., "Pharmacokinetics and Pharmacodynamics of Midazolam and Metabolites in Nonventilated Infants After Craniofacial Surgery", Anesthesiology, 105(6):1135-46, (2006).

Perrine, S. P., (2008) 'Fetal Globin Stimulant Therapies in the Beta-Hemoglobinopathies: Principles and Current Potential,' Pediatr Ann 37(5):339-346.

Phuphanich, S. et al., Oral Sodium Phenylbutyrate in Patients with Recurrent Malignant Gliomas: A Dose Escalation and Pharmacologic Study, Neuro-Oncology 177 (2005).

Piscitelli, S.C. et al. (1995). 'Disposition of Phenyl butyrate and its Metabolites, Phenylacetete and Phenylacetylglutamine,' J. Clin. Pharmacal. 35:368-373.

Praphanproj, V. et al., Three Cases of Intravenous Sodium Benzoate and Sodium Phenylacetate Toxicity Occurring in the Treatment of Acute Hyperammonemia, 23 J. Inherited Metabolic Disease 129-136 (2000).

Priester, T. et al., "Hyperammonemia from a Urea Cycle Disorder Presenting in Adulthood", Open Critical Care Medicine Journal, 2009; 2:9-12.

Product Monograph including patient medication information RAVICTI; Mar. 16,, 2016 (Year: 2016), 28 pages.

Propst, A. et al, 'Prognosis and Lite Expectancy in Chronic Liver Disease', 40 Dig Dis Sci 1805 (1995) (Abstract Only).

RAVICTI (glycerol phenylbutyrate) oral liquid, US Prescribing Information 2013.

RAVICTI (glycerol phenylbutyrate) oral liquid, US Prescribing Information 2016.

Riley, T.R. et al. (Nov. 15, 2001). 'Preventive Strategies in Chronic Liver Disease: Part II. Cirrhosos,' Am. Fam. Physician 64(10):1735-1740. (Abstract Only).

Rockey, D. C., et al., 'Randomized, Controlled, Double Blind Study of Glycerol Phenylbutyrate in Patients with Cirrhosis and Episodic Hepatic Encephalopathy,' Hepatology 56:248(a) (2012), 1 pge.

Rose CF, Ammonia-lowering strategies for the treatment of hepatic encephalopathy, Clin Pharmacol Ther. Sep. 2012;92(3):321-31.

Rudman, D., et al., Maximal Rates of Excretion and Synthesis of Urea in Normal and Cirrhotic Subjects, 52 J. Clin. Invest. 2241-2249 (1973).

Ruvoen-Clouet et al., Biochem J. 393: 627-634, 2006.

Ryu, H, et al, (2005) 'Sodium Phenylbutyrate Prolongs Survival and Regulates Expression of Anti-Apoptotic Genes in Transgenic Amyotrophic Lateral Sclerosis Mice,' J Neurochem 93:1087-1098.

Salam, M, et al, 'Modified-Orientation Log to Assess Hepatic Encephalopathy,' Aliment Pharmacol Ther. 35(8):913-920 (2012).

Scientific Discussion for Ammonaps, EMEA 2005, available at http://www.ema.europa.eu/docs/enGB/document_library/EPAR-ScientificDiscussion/human/000219/WC500024748.pdf, 12 pgs.

Scottish Medicines Consortium, Carglumic Acid 200 mg Dispersible Tablets (Carbaglu) No. 299/06 (Sep. 8, 2006), 5 pgs.

Seakins, J.W.T., The Determination of Urinary Phenylacetylglutamine as Phenylacetic Acid: Studies on its Origin in Normal Subjects and Children with Cystic Fibrosis, 35 Clin. Chim. Acta.121-131 (1971).

Search and Examination Report for British Patent Application No. GB 0915545.8, dated Oct. 8, 2009, 5 pages.

Sherwin, C. et al., The Maximum Production of Glutamine by the Human Body as Measured by the Output of Phenylacetylglutamine, 37 J. Biol. Chem. 113(1919).

Shin Jang-Woo etal., Interpretation of Animal Dose and Human Equivalent Dose for Drug Development, The Journal of Korean Oriental Medicine, vol. 31. No. 3., 2010, pp. 1-7.

Shiple, G.J. et al., Synthesis of Amino Acids in Animal Organisms. I. Synthesis of Glycocoll and Glutamine in the Human Organism, 44 J. Am. Chem. Soc. 618-624 (1922).

Sias et al., Biochemistry 43: 10138-10148, 2004.

Simell, O et al: 'Waste nitrogen excretion via amino acid acylation: Benzoate and phenylacetate in lysinuric protein intolerance' Pediatric Research, Williams and Wilkins, Baltimore, MD, US, vol. 20, No. 11, Jan. 1, 1986 (Jan. 1, 1986-), pp. 1117-1121, XP009127277 ISSN: 0031-3998.

Singh, "Consensus Statement from a Conference for the Management of Patients with Urea Cycle Disorders", 138 J. Pediatrics S1-S5 (2001).

Smith, W., et al., "Ammonia Control in Children Ages 2 Months through 5 Years with Urea Cycle Disorders: Comparison of Sodium Phenylbutyrate and Glycerol Phenylbutyrate," J Pediatr. 162(6):1228-1234.e1 (2013).

South San et al, 'Hyperion Therapeutics Announces Presentation of Long Term Data on Ammonia Control in Pediatric Patients Treated With Ravicti(R) at the 12th International Congress of Inborn Errors of Metabolism and the Urea Cycle Disorder Satellite Symposium', (Sep. 3, 2013), URL: http://files.shareholder.com/downloads/AMDA-1412CE/0x0x688110/4e684e9d-6c54-4963-a993-72c90f308802/HPTX_News_2013_9_3_General_Releases.pdf, (Mar. 21, 2016), XP055260208.

Spreadsheet showing impurity levels for various batches of RAVICTI®.

Stauch et al., 'Oral L-ornithine-L-aspartate therapy of chronic hepatic encephalopathy: results of a placebo-controlled double-blind study', Journal of Hepatology, vol. 28, No. Issue, (May 1998), pp. 856-864, URL: http://www.sciencedirect.com, XP055250053.

Summar, M. and Tuchman, M., Proceedings of a Consensus Conference for the Management of Patients with Urea Cycle Disorders, 138 J. Pediatrics S6-S10 (2001).

Summar, M. et al., 'Description and Outcomes of 316 Urea Cycle Patients From a 21-Year, Multicenter Study of Acute Hyperammonemic Episodes', Abstract, presented at Annual Symposium CCH-Congress Centre Hamburg, Sep. 4-7, 2007, GSSIEM 2007, two pages.

Summar, M. et al., Unmasked Adult-Onset Urea Cycle Disorders in the Critical Care Setting, 21 Crit. Care Clin. S1-S8 (2005).

Summar, M., Current Strategies for the Management of Neonatal Urea Cycle Disorders, 138 J. Pediatrics S30-S39 (2001).

Summar, M., Urea Cycle Disorders Overview, Gene Reviews, www.genetests.org (Apr. 2003), 15 pgs.

Summar, M.L. et al., Diagnosis, Symptoms, Frequency and Mortality of 260 Patients with Urea Cycle Disorders From a 21-Year, Multicentre Study of Acute Hyperammonemic Episodes, 97 Acta Paediatr. 1420-1425 (Oct. 2008, e-pub. Jul. 17, 2008).

Sushma, S. et al., 'Sodium Benzoate in the Treatment of Acute Hepatic Encephalopathy: A Randome Double-blind Trial,' Hepatology, 16 (1992), 138-144.

Swedish Orphan International, 'Urea Cycle Disorders an International Perspective', Poster, Symposium Swedish Orphan International, Barcelona, Spain, Jan. 12, 2007, one page. (2007).

Tanner, L. M., et al., Nutrient Intake in Lysinuric Protein Intolerance, 30 J. Inherit. Metab. Dis. 716 (2007), 716-721.

The Doctors Company webpage; retreived Oct. 4, 2018 (Year: 2018); 2 pages.

The National Organization for Rare Disorders (2012). The Physician's Guide to Urea Cycle Disorders, at http://nordphysicianguides.org/wp-content/uploads/2012/02/NORD_Physician_Guide_to_Urea_Cycle_Disorders.pdf, 28 pgs.

Thibault, A., et al., 'A Phase I and Pharmacokinetic Study of Intravenous Phenylacetate in Patients with Cancer,' Cancer Res. 54:1690-1694 (1994).

Thibault, A., et al., 'Phase I Study of Phenylacetate Administered Twice Daily to Patients with Cancer,' Cancer 75:2932-2938 (1995).

(56) References Cited

OTHER PUBLICATIONS

Thompson, P. 'Pharmacokinetics of phenyacetate administered as a 30-min infusion in children with refractory cancer', Cancer Chemother. Pharmacol. 2003, 52: 417-423.
Todo, S. et al., Orthotopic Liver Transplantation for Urea Cycle Enzyme Deficiency, 15 Hepatology 419-422 (1992).
Tuchman, M. et al. (2008, e-pub. Jun. 17, 2008). 'Cross-Sectional Multicenter Study of Patients With Urea Cycle Disorders in the United States,' Malec. Genetics Metab. 94:397-402.
Tuchman, M., and Yudkoff, M., Blood Levels of Ammonia and Nitrogen Scavenging Amino Acids in Patients with Inherited Hyperammonemia, 66 Molecular Genetics and Metabolism 10-15 (1999).
UMass Memorial Medical Center, Lab Updates, 'Measurement of Ammonia in Blood.' Feb. 2007. Accessed at www.ummlabs.org/News/07Feb.pdf, 3 pgs.
Uribe, M. et al., "Hyperammonemic Hepatic Encypholopathy Treated with Sodium Benzoate, Final report of double blind evaluation", Instituto Nacional de la Nutricion, Mexico D.F., Hepatology, 10(4):589, (1989).
Vierling JM etal., Fasting Blood Ammonia Predicts Risk and Frequency of Hepatic Encephalopathy Episodes in Patients With Cirrhosis, Clin Gastroenterol Hepatol. Jun. 2016;14(6):903-906.
Vilstrup, H, et al, 'Hepatic Encephalopathy in Chronic Liver Disease: 2014 Practice Guideline by the American Association for the Study of Liver Diseases and the European Association for the Study of the Liver,' Hepatology 60 (2):715-735 (2014).
VKM Report 2016:66 used as evidentiary reference (Year: 2016).
Walsh et al., Chemical Abstract vol. 112, No. 231744, 1990, 1 page.
Walsh et al., The Journal of Biological Chemistry, vol. 265, No. 8, pp. 4374-4381 (1990), sn-1,2-Diacylgylcerol Kinase of *Escherichia coli*.
Waterlow, J.C., The Partition of Nitrogen in the Urine of Malnourished Jamaican Infants, 12 Am. J. of Clin. Nutrition 235-240 (1963).
Welbourne, T. et al., 'The Effect of Glutamine Administration on Urinary Ammonium Excretion in Normal Subjects and Patients with Renal Disease', 51 J. Clin. Investigation 1852 {1972).
Wilcken, B, 'Problems in the Management of Urea Cycle Disorders', 81 Molecular Genetics and Metabolism 85 (2004).
Wilson, C.J, et al, 'Plasma Glutamine and Ammonia Concentrations in Ornithine Carbamoyltransferase Deficiency and Citrullinaemia', 24 J. Inherited Metabolic Disease 691 (2001).
Wright, G., et al., Management of Hepatic Encephalopathy, 2011 International Journal of Hepatology 1 (2011), 11 pgs.
Wright, P., Review: Nitrogen Excretion: Three End Products, Many Physiological Roles, 198 J. Experimental Biology 273-281 (1995).
Xiao et al., J Biol Chem. 286(30): 26353-26363, 2011.
Xie, G, et al, (2012) 'Role of Differentiation of Liver Sinusoidal Endothelial Cells in Progression and Regression of Hepatic Fibrosis in Rats,' Gastroenterology 142:S918.
Yajima, et al. 'Diurnal Fluctuations of Blood Ammonia Levels in Adult-Type Citrullinemia', 137 Tokohu J. Ex/ Med, 213-220 (1982).
Yu, Ryan and Potter, Murray, 'Diagnosis of Urea Cycle Disorders in Adulthood: Late- Onset Carbamyl Phosphate Synthetase 1 Deficiency', 7 MUMJ 30 (2010).
Yudkoff, M. et al., In Vivo Nitrogen Metabolism in Ornithine Transcarbamylase Deficiency, 98 J. Clin. Invest. 2167-2173 (1996).
Yurdaydin C., Blood ammonia determination in cirrhosis: Still confusing after all these years? Hepatology 38 (5) Nov. 2003, pp. 1307-1310.
Zeitlin, P., Novel Pharmacologic Therapies for Cystic Fibrosis, 103 J. Clinical Investigation 447 (1999).
Zeitlin, P.L. et al. (2002) 'Evidence of CFTR Function in Cystic Fibrosis After System Administration of 4-Phenylbutyrate,' Mol Therapy 6(1 ):119-126.
Zhao, et al., "Oxidation of Primary Alcohols to Carboxylic Acids with Sodium Chlorite Catalyzed by TEMPO and Bleach," J. Org. Chem., 1999, 64 (7), pp. 2564-2566.

* cited by examiner

PROCEDURE FOR THE PREPARATION OF 4-PHENYL BUTYRATE AND USES THEREOF

This application is a continuation of U.S. patent application Ser. No. 15/696,448, filed Sep. 6, 2017, which is a continuation of U.S. patent application Ser. No. 15/164,126, filed May 25, 2016, now U.S. Pat. No. 9,914,692, the disclosures of which are incorporated herein by reference in their entireties.

The oxidation of primary alcohols to carboxylic acids is a transformation of broad utility in synthetic chemistry. Commonly used methods include the use of chromium (VI) oxide in sulfuric acid, ruthenium (III) chloride with $H_5IO_6$ and Swern oxidation of the alcohol to the aldehyde, followed by oxidation of the aldehyde with $NaClO_2$. These methods suffer from disadvantages such as the disposal issues relating to the use of metals, and the generation of equimolar amounts of sulfides in the Swern procedure.

TEMPO, i.e., 2,2,6,6,-tetramethyl-1-piperdinyloxy, free radical, together with sodium hypochlorite (NaClO) also can be used for oxidation. A variant of the TEMPO procedure, a one-step procedure using sodium chlorite in the presence of a catalytic amount of TEMPO and sodium hypochlorite which reduces the epimerization of any α-chiral centers, has been described.

4-Phenyl-1-butyrate, which may be prepared by oxidation of 4-phenyl-1-butanol, is a useful intermediate for the preparation of glycerol phenylbutyrate (glycerol tri-[phenylbutyrate]; HPN-100). Glycerol phenylbutyrate is a nitrogen-scavenging drug for the treatment of nitrogen retention disorders such as urea cycle disorders and hepatic encephalopathy.

Provided is a process for the preparation of 4-phenyl-1-butyric acid comprising: oxidizing 4-phenyl-1-butanol with sodium chlorite, a nitroxyl radical catalyst, and sodium hypochlorite in an organic solvent and a phosphate buffer and quenching the reaction by the addition of sodium sulfite.

Also provided is 4-phenyl-1-butyric acid prepared by a process described herein.

Also provided is a process for converting 4-phenyl-1-butyric acid prepared as described herein to glycerol triphenylbutyrate comprising: converting 4-phenyl-1-butyric acid prepared by the process disclosed herein to 4-phenyl-1-butyryl chloride; and reacting the 4-phenyl-1-butyryl chloride with glycerol in an organic solvent in the presence of a suitable base.

Also provided is glycerol triphenylbutyrate prepared by a process described herein.

These and other aspects of the invention disclosed herein will be set forth in greater detail as the patent disclosure proceeds.

Provided is a process for the preparation of 4-phenyl-1-butyric acid comprising: reacting 4-phenyl-1-butanol with sodium chlorite, a nitroxyl radical catalyst, and sodium hypochlorite in an organic solvent and a phosphate buffer; and quenching the reaction with sodium sulfite to produce 4-phenyl-1-butyric acid.

In some embodiments, reacting 4-phenyl-1-butanol with sodium chlorite, a nitroxyl radical catalyst and sodium hypochlorite in an organic solvent and a phosphate buffer comprises sequentially adding sodium chlorite and sodium hypochlorite to a mixture of 4-phenyl-1-butanol and a nitroxyl radical catalyst in an organic solvent and a phosphate buffer.

In some embodiments, reacting 4-phenyl-1-butanol with sodium chlorite, a nitroxyl radical catalyst and sodium hypochlorite in an organic solvent and a phosphate buffer comprises dissolving 4-phenyl-1-butanol and a catalytic amount of a nitroxyl radical catalyst, together with a catalytic amount of sodium hypochlorite in the organic solvent to form a solution and then adding the phosphate buffer to the solution. In some embodiments, the dissolution is conducted at ambient temperature with stirring.

In some embodiments, reacting 4-phenyl-1-butanol with sodium chlorite, a nitroxyl radical catalyst, and sodium hypochlorite in an organic solvent and a phosphate buffer comprises adding an aqueous solution of sodium chlorite and a catalytic amount of sodium hypochlorite while maintaining the temperature of the reaction mixture at 20-25° C.

In some embodiments, the method further comprises adjusting the pH of the reaction mixture to about 9.8 with aqueous sodium hydroxide prior to quenching the reaction.

In some embodiments, the nitroxyl radical catalyst is chosen from a TEMPO catalyst and an AZADO catalyst or a mixture thereof.

In some embodiments, the TEMPO catalyst is chosen from (2,2,6,6-tetramethyl-1-piperidinyloxy, free radical), 4-MeO-TEMPO (4-methoxy-2,2,6,6-tetramethylpiperidine-1-oxyl); 4-acetoamido-TEMPO (4-acetamido-2,2,6,6-tetramethylpiperidine-1-oxyl), and 4-hydroxy-TEMPO (4-hydroxy-2,2,6,6-tetramethylpiperidine-1-oxyl).

In some embodiments, the TEMPO catalyst is polymer-supported.

In some embodiments, the AZADO catalyst is chosen from 2-azaadamantane N-oxyl (AZADO), 1-methyl-2-azaadamantane-N-oxyl (1-Me-AZADO), and 9-azanoradamantane N-oxyl (Nor-AZADO).

In some embodiments, the nitroxyl radical catalyst is 9-azabicyclo[3.3.1]nonane N-oxyl (ABNO).

In some embodiments, the organic solvent is selected from acetonitrile, tetrahydrofuran, 2-methyltetrahydrofuran, diethyl ether, methyl tert-butyl ether, dimethoxyethane, 2-methoxyethyl ether (diglyme), triethylene glycol dimethyl ether (triglyme), toluene, benzene, hexane, pentane, dioxane, and mixtures thereof.

In some embodiments, the organic solvent is acetonitrile.

In some embodiments, the phosphate buffer comprises an aqueous solution of potassium phosphate monobasic and potassium phosphate dibasic.

In some embodiments, the potassium phosphate monobasic and potassium phosphate dibasic are each used in amounts of about 0.5 equivalent to about 1.5 equivalents. In some embodiments, the potassium phosphate monobasic and potassium phosphate dibasic are each used in amounts of about 1.1 equivalents to about 1.5 equivalents.

In some embodiments, the amount of the nitroxyl radical catalyst used is about 1.0 to about 50.0 mol percent. In some embodiments, the amount of the nitroxyl radical catalyst used is about 1.0 to about 10.0 mol percent. In some embodiments, the amount of the nitroxyl radical catalyst used is about 5.0 to about 10.0 mol percent. In some embodiments, the amount of the nitroxyl radical catalyst used is about 7.0 mol percent.

In some embodiments, the amount of sodium chlorite used is about 1 equivalent to about 3 equivalents. In some embodiments, the amount of sodium chlorite used is about 1.5 equivalent to about 2 equivalents. In some embodiments, the amount of sodium chlorite used is about 1.7 equivalents.

In some embodiments, the sodium sulfite is aqueous sodium sulfite.

In some embodiments, the sodium sulfite is solid sodium sulfite.

In some embodiments, the amount of sodium sulfite used is about 1 to about 3 equivalents. In some embodiments, the amount of sodium sulfite used is about 2.4 to 2.5 equivalents.

Also provided is 4-phenyl-1-butyric acid prepared by a process described herein.

In some embodiments, the 4-phenyl-1-butyric acid prepared by a process described herein does not require further purification.

In some embodiments, the process further comprises adding aqueous HCl to the quenched reaction to adjust the pH to about pH 3; and collecting the 4-phenyl-1-butyric acid by filtration.

In some embodiments, the process further comprises adding adding aqueous HCl to the quenched reaction to adjust the pH to about pH 6.5; adding a seed crystal of 4-phenyl-1-butyric acid; and collecting the formed 4-phenyl-1-butyric acid by filtration.

In some embodiments, the 4-phenyl-1-butyric acid prepared by a process described herein is greater than about 80% pure by weight. In some embodiments, the 4-phenyl-1-butyric acid prepared by a process described herein is greater than about 85% pure by weight. In some embodiments, the 4-phenyl-1-butyric acid prepared by a process described herein is greater than about 90% pure by weight. In some embodiments, the 4-phenyl-1-butyric acid prepared by a process described herein is greater than about 93% pure by weight.

In some embodiments, the 4-phenyl-1-butyric acid prepared by a process described herein is greater than about 80% pure by high performance liquid chromatography (HPLC) analysis. In some embodiments, the 4-phenyl-1-butyric acid prepared by a process described herein is greater than about 85% pure by high performance liquid chromatography (HPLC) analysis. In some embodiments, the 4-phenyl-1-butyric acid prepared by a process described herein is greater than about 90% pure by high performance liquid chromatography (HPLC) analysis. In some embodiments, the 4-phenyl-1-butyric acid prepared by a process described herein is greater than about 95% pure by high performance liquid chromatography (HPLC) analysis. In some embodiments, the 4-phenyl-1-butyric acid prepared by a process described herein is greater than about 97% pure by high performance liquid chromatography (HPLC) analysis. In some embodiments, the 4-phenyl-1-butyric acid prepared by a process described herein is greater than about 98% pure by high performance liquid chromatography (HPLC) analysis. In some embodiments, the 4-phenyl-1-butyric acid prepared by a process described herein is greater than about 99% pure by high performance liquid chromatography (HPLC) analysis.

In some embodiments, the process further comprises purifying the 4-phenyl-1-butyric acid.

Also provided is a process for converting 4-phenyl-1-butyric acid prepared as described herein to glycerol triphenylbutyrate comprising esterifying glycerol with three molecules of 4-phenyl-1-butyric acid. In some embodiments the process for converting 4-phenyl-1-butyric acid prepared as described herein to glycerol triphenylbutyrate comprises: converting 4-phenyl-1-butyric acid prepared by the process disclosed herein to 4-phenyl-1-butyryl chloride; and reacting the 4-phenyl-1-butyryl chloride with glycerol in an organic solvent in the presence of a suitable base.

4-Phenyl-1-butyric acid may be conveniently converted to the corresponding acid chloride by any of the means known to those skilled in the art of synthesis. In some embodiments, the conversion of 4-phenyl-1-butyric acid or a salt thereof to the acid chloride is done by reacting 4-phenyl-1-butyric acid or a salt thereof with thionyl chloride.

In some embodiments, the base for the reaction of 4-phenyl-1-butyryl chloride with glycerol is selected from triethylamine, imidazole, 1-methylimidazole, and 1-ethylimidazole.

In some embodiments, the solvent for the reaction of 4-phenyl-1-butyryl chloride with glycerol is selected from tetrahydrofuran, dichloromethane, chloroform, carbon tetrachloride, and ethylenedichloride.

Also provided is glycerol triphenylbutyrate prepared by a process described herein.

Also provided is a pharmaceutical composition comprising glycerol triphenylbutyrate prepared by a process described herein. In some embodiments the pharmaceutical composition does not include any pharmaceutically acceptable excipients. In some embodiments the pharmaceutical composition comprises one or more pharmaceutically acceptable excipients.

Also provided is a method for treating a subject with a nitrogen retention disorder comprising administering to the subject glycerol triphenylbutyrate prepared by a process described herein.

In some embodiments, the nitrogen retention disorder is selected from urea cycle disorders and hepatic encephalopathy. In some embodiments, the nitrogen retention disorder is a urea cycle disorder.

In some embodiments, the subject to be treated is a human patient. In some embodiments, the human patient is an adult. In some embodiments, the human patient is a pediatric subject 12 to 18 years of age. In some embodiments, the human patient is a pediatric subject under the age of 12.

In some embodiments, the glycerol triphenylbutyrate is administered orally. In some embodiments, the glycerol triphenylbutyrate is administered directly into the mouth via oral syringe or dosing cup. In some embodiments, the glycerol triphenylbutyrate is administered by nasogastric tube or gastrostomy-tube.

In some embodiments, the glycerol triphenylbutyrate is administered with food.

In some embodiments, the method for treating a subject with a urea cycle disorder comprises administering to the subject glycerol triphenylbutyrate prepared by a process described herein in a dosage of about 5.33 to 8.79 g/m$^2$/day. In some embodiments, the dosage is at or about 6 to 8 g/m$^2$/day, 6.5 to 7.5 g/m$^2$/day, 7.0 to 7.3 g/m$^2$/day, or 7.15 to 7.25 g/m$^2$/day. In some embodiments, the effective dosage is at or about 7.18 or 7.05 g/m$^2$/day.

The following examples serve to more fully describe the disclosed compounds the methods. It is understood that these examples in no way serve to limit the true scope of this invention, but rather are presented for illustrative purposes.

EXAMPLES

The following non-limiting examples are illustrative of certain embodiments of the present invention. The following abbreviations are used:
TEMPO: 2,2,6,6-tetramethyl-1-piperidinyloxy, free radical
MTBE: methyl tert-butyl ether
4-PBA: 4-phenyl-1-butyric acid
3-BPA: 3-benzoyl propionic acid

Example 1

Preparation of 4-phenyl-1-butyric Acid

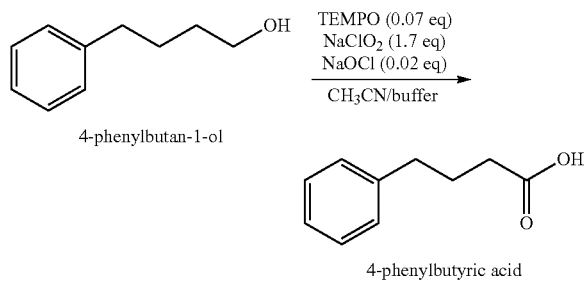

In a 50 L jacketed reactor, equipped with a Huber Unistadt 360 chiller, 4-phenyl-1-butanol (1 kg, 6.66 mol) and TEMPO (72.8 g, 466 mmol, 0.07 eq.) were dissolved in acetonitrile (5 L) at ambient temperature. In a 12 L 3-neck round bottom flask, a potassium phosphate buffer was prepared by dissolving potassium phosphate monobasic (996 g, 7.32 mol) and potassium phosphate dibasic (1276 g, 7.33 mol) in water (10 L), and the prepared buffer was transferred into the reaction mixture at ambient temperature. Two other solutions were prepared separately including an aqueous solution of sodium chlorite by dissolving sodium chlorite (1.28 kg, 11.32 mol, 1.7 eq.) in water (4 L) and bleach solution by diluting 8.25% bleach (110 mL, 122 mmol, 0.02 eq.) in water (200 mL). The temperature of the reaction mixture was adjusted to 10-40° C. followed by adding the prepared aqueous solution of sodium chlorite (900 mL) and the diluted bleach (60 mL) in sequence. The remaining of the two solutions was then slowly added simultaneously and separately over four hours while maintaining the temperature of the reaction mixture at 10-40° C. It was noted that after the addition, the temperature of the reaction mixture kept increasing to 30° C., and maintained at 30° C. for about two hours before starting to slowly cool down to 20° C. The mixture was agitated at 20° C. overnight, and the conversion was >99.9%. Temperature of the reaction mixture was adjusted to below 0-20° C. followed by pH adjustment to 9.8 with 25% aqueous sodium hydroxide (prepared from 50% aqueous sodium hydroxide with water, 1/1 v/v; ~1360 mL). An aqueous solution of sodium sulfite was prepared by dissolving sodium sulfite (2 kg, 15.87 mol, 2.4 eq.) in water (10 L), and slowly transferred into reaction mixture over one hour while maintaining the temperature at below 15° C. (note that the peak for 3-PBA increases to about 6-7 A % immediately after the sodium sulfite quench). The resulting light cloudy mixture was stirred at 15 to 30° C. overnight (to bring the levels of the 3-PBA peak back down to about 1.5 A %) and then cooled to 0-10° C. (to maximize precipitation of the inorganic salts). The suspension was stirred at 0-10° C. for two hours and then the solids removed by filtration through a Celite® pad (250 g). The filtered cake was washed with cold water (1 L×3). The combined filtrate was washed with MTBE (10+5 L). The resulting colorless aqueous phase was cooled to 0-10° C., and agitated overnight (no further precipitation of inorganic material was noted). It is essential to perform the acidification on a chilled solution, in order for the 4-PBA to precipitate. To the chilled solution was slowly added 6N aqueous HCl (1 L) over two hours to adjust pH to about 6.5. At this stage, 4-PBA seed (10 g, 60.9 mmol) was added to induce crystallization to form a thin suspension. Additional 6N aqueous HCl (2.6 L) was slowly added over two hours to adjust the pH to 3. The resulting suspension was agitated at 5° C. overnight, and then filtered to collect the solid. The wet cake was washed with ice cold water (2 L), and dried under vacuum with nitrogen purge to provide 4-PBA as white solid, which was dried in the open air, in glass trays over 3 days.

The total amount of the crude 4-PBA was 1034.1 g (94.6% isolation yield) with 99.7 A % purity by HPLC analysis, 210 nm and >99 A % by 260 nm (1 mg/mL acetonitrile solution). No 3-BPA was detected by both wavelengths. DSC analysis gave the melting point 52° C.

Next, the 4-PBA was analyzed by HPLC using with the concentration of 5 mg/mL in mobile phase A and acetonitrile (80/20 v/v). The purity was 99.7 A % with 93% w/w. Under this analysis 3-PBA was identified in 0.04 A % along with four other impurities in the range of 0.04 to 0.1 A %. The weight assay of 3-PBA was calculated as 0.002% w/w using 0.04% 3-BPA solution. Final Karl Fischer analysis was 0.14% w/w of water content.

Those skilled in the art will recognize that various modifications, additions, substitutions, and variations to the illustrative examples set forth herein can be made without departing from the spirit of the invention and are, therefore, considered within the scope of the invention.

We claim:

1. A composition comprising 4-phenyl-1-butyric acid and less than 0.04% 3-benzoyl propionic acid w/w as measured by area percentage of HPLC.

2. The composition of claim 1, wherein the 4-phenyl-1-butyric acid is prepared by a process comprising:
   reacting 4-phenyl-1-butanol with sodium chlorite, a nitroxyl radical catalyst and sodium hypochlorite in an organic solvent and a phosphate buffer; and quenching the reaction with sodium sulfite.

3. The composition of claim 1, wherein the 4-phenyl-1-butyric acid is greater than about 90% pure by weight.

4. The composition of claim 1, wherein the 4-phenyl-1-butyric acid is greater than about 90% pure by high performance liquid chromatography (HPLC) analysis.

5. The composition of claim 1, wherein the 4-phenyl-1-butyric acid has a melting point of 52° C. as determined by differential scanning calorimetry (DSC) analysis.

* * * * *